US00PP13084P2

(12) United States Plant Patent
Bartels

(10) Patent No.: US PP13,084 P2
(45) Date of Patent: Oct. 15, 2002

(54) VERONICA PLANT NAMED 'BARNINETEEN'

(75) Inventor: Gosen B. H. Bartels, Aalsmeer (NL)

(73) Assignee: Bartels Breeding B.V., Aalsmeer (NL)

( * ) Notice: Subject to any disclaimer, the term of this patent is extended or adjusted under 35 U.S.C. 154(b) by 9 days.

(21) Appl. No.: 09/840,805

(22) Filed: Apr. 25, 2001

(51) Int. Cl.[7] ..... A01H 5/00
(52) U.S. Cl. ..... Plt./251
(58) Field of Search ..... Plt./251

(56) References Cited

PUBLICATIONS

UPOV–ROM GTITM Computer Database, GTI JOUVE Retrieval Software 2002/02, citation for 'Barninteen'.*

* cited by examiner

*Primary Examiner*—Bruce R. Campell
*Assistant Examiner*—Wendy Couchoud Baker
(74) *Attorney, Agent, or Firm*—C. A. Whealy

(57) ABSTRACT

A new and distinct cultivar of Veronica plant named 'Barnineteen', characterized by its upright plant habit; glossy dark green leaves; freely flowering habit; dark violet blue-colored flowers; and good postproduction longevity.

1 Drawing Sheet

BOTANICAL CLASSIFICATION

*Veronica spicata.*

BACKGROUND OF THE INVENTION

The present Invention relates to a new and distinct cultivar of Veronica plant, botanically known as *Veronica spicata*, commercially used as a cut flower, and hereinafter referred to by the name 'Barnineteen'.

The new Veronica is a product of a planned breeding program conducted by the Inventor in Aalsmeer, The Netherlands. The objective of the breeding program was to create new freely-flowering Veronica cultivars with strong flower stems, and good postproduction longevity.

The new Veronica originated from a cross made by the Inventor in 1995 of the *Veronica spicata* cultivar Lilac Carina, not patented, as the female, or seed, parent and the *Veronica spicata* cultivar Blauriesin, not patented, as the male, or pollen, parent. The new Veronica was discovered and selected by the Inventor in 1996 as a flowering plant within the progeny of the stated cross in a controlled environment in Aalsmeer, The Netherlands. The selection of this new Veronica was based on its dark violet blue flower color.

Asexual reproduction of the new cultivar by vegetative cuttings taken at Aalsmer, The Netherlands since 1996, has shown that the unique features of this new Veronica are stable and reproduced true to type in successive generations.

SUMMARY OF THE INVENTION

Plants of the cultivar Barnineteen have not been observed under all possible environmental conditions. The phenotype may vary somewhat with variations in environment such as temperature, light intensity, daylength, water status, and fertilizer type or rate without, however, any variance in genotype.

The following traits have been repeatedly observed and are determined to be the unique characteristics of 'Barnineteen'. These characteristics in combination distinguish 'Barnineteen' as a new and distinct cultivar:

1. Upright plant habit.
2. Glossy dark green leaves.

3. Freely flowering habit.
4. Dark violet blue-colored flowers.
5. Good postproduction longevity.
6. Resistant to Downy Mildew.

Compared to plants of the female parent, the cultivar Lilac Carina, plants of the new Veronica have glossier leaves and darker colored flowers. Compared to plants of the male parent, the cultivar Blauriesin, plants of the new Veronica have a higher percentage of male sterile flowers, have darker colored flowers and better postproduction longevity.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Veronica. The photograph comprises a side perspective view of typical flowering stems of 'Barnineteen'.

DETAILED BOTANICAL DESCRIPTION

The following observations, measurements and values describe plants of the new cultivar grown in a glass-covered greenhouse in Aalsmeer, The Netherlands. During the production of the plants, day temperatures ranged from 18 to 25° C. and night temperatures ranged from 15 to 18° C. Plants were planted in ground beds in the early spring, pinched about 2 weeks later, and grown for about six months at which time the photographs and the detailed botanical description were made. Color references are made to The Royal Horticultural Society Colour Chart except where general terms of ordinary dictionary significance are used.

Botanical classification: *Veronica spicata* cultivar Barnineteen.

Parentage:

*Female parent.*—*Veronica spicata* cultivar Lilac Carina, not patented.

*Male parent.*—*Veronica spicata* cultivar Blauriesin, not patented.

Propagation:

*Type cutting.*—Vegetative cuttings.

*Time to initiate roots.*—Summer: About 7 days at 20° C. Winter: About 10 days at 18° C.

*Time to produce a rooted cutting or liner.*—Summer: About 14 days at 20° C. Winter: About 20 days at 18° C.

*Root description.*—White, fine, fibrous.

*Rooting habit.*—Freely branching, dense.

Plant description:

*Form.*—Upright, tall, columnar.

*Usage.*—Cut flower.

*Crop time.*—From rooted cuttings, about 12 weeks are required to produce flowering plants.

*Plant height.*—About 80 cm.

*Area of spread.*—About 30 cm.

*Vigor.*—Moderately vigorous.

*Branching habit.*—Greenhouse-grown plants: When pinched, about 20 flowering stems develop per plant. Field-grown plants: When pinched, about 10 flowering stems develop per plant.

*Lateral branches.*—Length: About 80 cm. Diameter: About 5 mm. Internode length: About 2 cm. Strength: Strong. Aspect: Erect. Texture: Smooth, glabrous. Color: 141B.

*Foliage description.*—Leaves simple, opposite, generally symmetrical, durable and long persisting. Length: About 10 cm. Width: About 3 cm. Shape: Lanceolate. Apex: Acuminate. Base: Attenuate. Margin: Sharply serrate. Texture, both surfaces: Smooth, glabrous. Venation pattern: Pinnate. Color: Young foliage, upper surface: 141A, glossy. Young foliage, lower surface: 139B. Mature foliage, upper surface: 139A, glossy. Mature foliage, lower surface: 139B. Venation, upper surface: 139A. Venation, lower surface: 139B. Petiole: Length: About 5 mm. Diameter: About 1.5 mm. Texture, both surfaces: Smooth. Color: 139A to 139B.

Flower description:

*Flower type and habit.*—Single campanulate dark violet blue-colored flowers arranged in upright racemes; flowers face mostly outward. Flowers not persistent. Racemes about 20 cm in length and about 2 cm in diameter.

*Natural flowering season.*—Flowering continuous during the summer in Aalsmeer, The Netherlands.

*Quantity of flowers.*—Freely flowering with four flowering racemes per lateral branch and about 150 open flowers and flower buds per raceme.

*Fragrance.*—Not detected.

*Flower longevity on the plant.*—About 10 days.

*Flower longevity as a cut flower.*—About 14 days.

*Flower buds.*—Length: About 3 mm. Diameter: About 2 mm. Shape: Ovoid. Color: 141C, becoming 94A with development.

*Corolla.*—Arrangement: Five-parted, petals fused at base, cupped or campanulate. Flower diameter: About 3 mm. Flower height (depth): About 3 mm. Petal length: About 3 mm. Petal width: About 2 mm. Petal shape: Deltoid. Petal apex: Acute. Petal margin: Entire. Texture: Smooth, glabrous. Petal color: When opening, upper and lower surfaces: 94A. Opened flower, upper and lower surfaces: 94A, fading to 94C with subsequent development.

*Calyx.*—Calyx length: About 1 mm. Calyx diameter: About 1 mm. Sepal arrangement: Five fused at base, campanulate. Sepal shape: Deltoid. Sepal apex: Acute. Sepal margin: Entire. Sepal texture, both surfaces: Smooth. Sepal color, both surfaces: 137A to 137B.

*Peduncle.*—Angle: About 80° from stem. Strength: Strong. Length: About 1 mm. Diameter: Less than 1 mm. Color: 141B.

*Reproductive organs.*—Most flowers are sterile due to male sterility. Stamens: Stamen quantity: One per flower. Anther shape: Oblong. Anther length: About 1 mm. Anther color: Green. Pollen amount: Scarce. Pollen color: Close to 4C. Pistils: Pistil quantity: One per flower. Pistil length: Less than 1 mm. Stigma shape: Spherical. Stigma color: Green. Style length: Less than 1 mm. Style color: Green. Ovary color: Close to 143C.

*Seed.*—Seed production has not been observed.

Disease/pest resistance: Plants of the new Veronica has been observed to be resistant to Downy Mildew.

It is claimed:

1. A new and distinct cultivar of Veronica plant named 'Barnineteen', as illustrated and described.

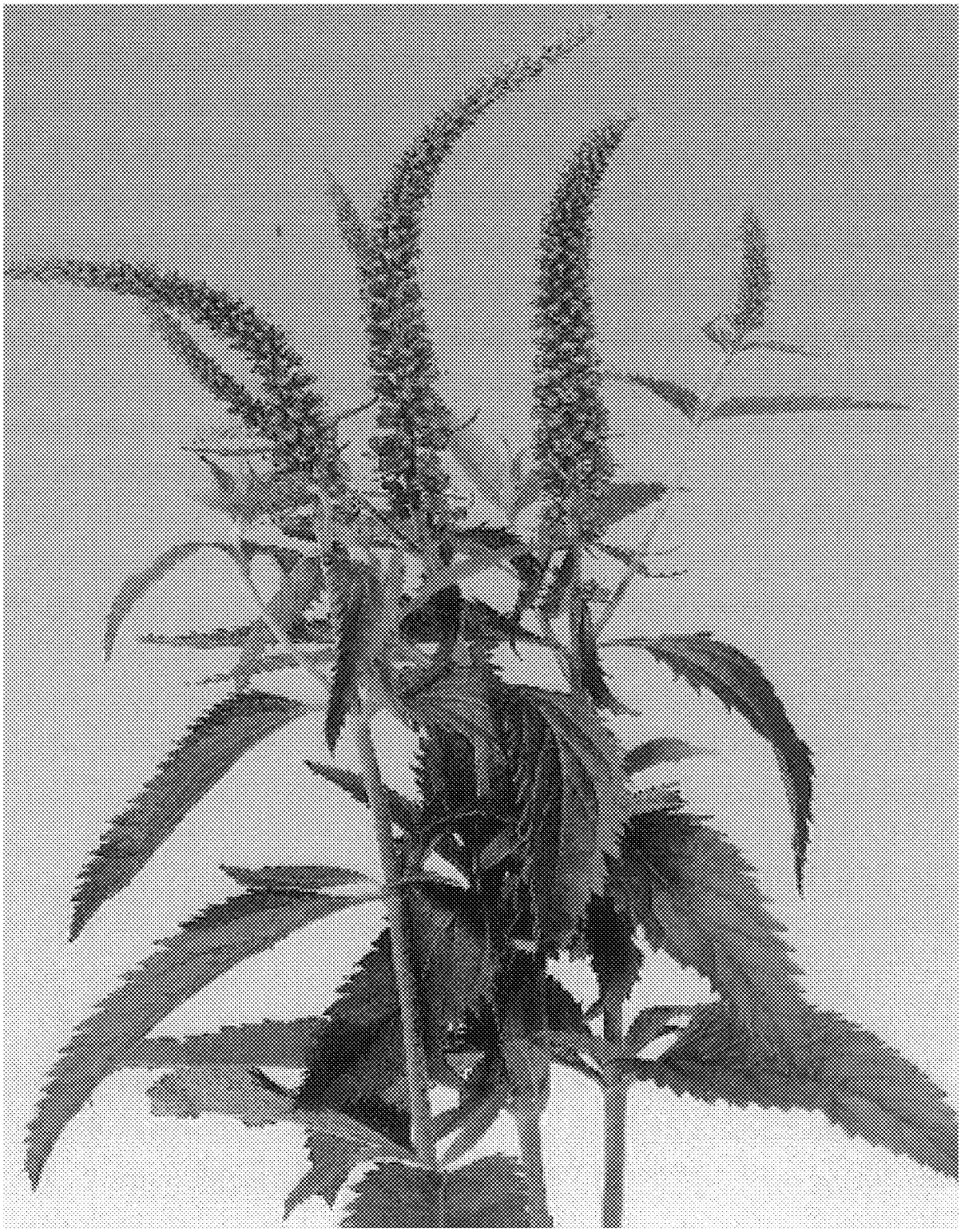

* * * * *